United States Patent
Rawlings

(10) Patent No.: US 8,652,081 B2
(45) Date of Patent: Feb. 18, 2014

(54) LUMBAR TRACTION DEVICE

(76) Inventor: Marcus Andrew Rawlings, Mildura (AU)

(*) Notice: Subject to any disclaimer, the term of this patent is extended or adjusted under 35 U.S.C. 154(b) by 173 days.

(21) Appl. No.: 12/740,494

(22) PCT Filed: Oct. 31, 2008

(86) PCT No.: PCT/AU2008/001628
§ 371 (c)(1),
(2), (4) Date: Oct. 4, 2010

(87) PCT Pub. No.: WO2009/055873
PCT Pub. Date: May 7, 2009

(65) Prior Publication Data
US 2011/0021961 A1     Jan. 27, 2011

(30) Foreign Application Priority Data
Nov. 1, 2007   (AU) ................. 2007905959

(51) Int. Cl.
*A61F 5/00*   (2006.01)
*A47C 31/00*  (2006.01)
*A47D 15/00*  (2006.01)
*B60R 21/00*  (2006.01)

(52) U.S. Cl.
USPC ............... 602/32; 602/19; 602/36; 482/907; 297/464; 297/485

(58) Field of Classification Search
USPC .......... 602/19, 32, 36, 13, 33, 34, 35, 37, 40, 602/5; 606/241, 237, 201, 202; 128/845, 128/875, 869, 874, 876, 95.1, 96.1, 99.1, 128/100.1; 601/23, 24, 33, 148, 151, 152; 297/464, 485; 482/55, 69, 54, 907, 43; 5/612, 621, 624
See application file for complete search history.

(56) References Cited

U.S. PATENT DOCUMENTS

| | | | |
|---|---|---|---|
| 4,622,957 A * | 11/1986 | Curlee | 602/13 |
| 4,881,528 A | 11/1989 | Scott | |
| 4,898,185 A | 2/1990 | Fuller | |
| 5,224,924 A * | 7/1993 | Urso | 602/19 |
| 6,045,519 A * | 4/2000 | Smith, Sr. | 602/13 |
| 6,315,750 B1 * | 11/2001 | Gray | 602/32 |
| 7,069,934 B2 * | 7/2006 | DiBella | 128/869 |

FOREIGN PATENT DOCUMENTS

CA    2118334 A1    4/1996

* cited by examiner

Primary Examiner — Victoria J Hicks
(74) Attorney, Agent, or Firm — The Webb Law Firm

(57) ABSTRACT

A lumbar traction device that can alleviate lower back pain is provided. The device includes a harness or girdle that is fitted about the torso region of a patient and an adjustable support assembly in the form of adjustable legs that allow the degree of traction to be adjusted by the patient. The device is safe and easy to use by a patient without constant medical supervision and is particularly suitable for use in domestic or office environments.

23 Claims, 5 Drawing Sheets

LUMBAR TRACTION DEVICE

FIELD OF THE PRESENT INVENTION

The present invention relates to the field of orthotics, and in particular, to the field of orthotic devices that can alleviate lower back pain by reducing the load on a person's back.

BACKGROUND OF THE PRESENT INVENTION

Back pain may be caused by many conditions including bulging, ruptured or herniated discs between vertebrae in the lumbar region of a patient's spine. Such conditions are treated by means of either invasive surgery which has inherent risks or less invasive manipulative techniques. Temporary and permanent pain relief can be achieved using traction devices which are widely used by clinicians such as physiotherapists during patient consultations. One of the shortcomings of the traction devices used by clinicians is that they are often large and expensive, making these devices unsuitable for home use.

An example of the traction device suitable for home use is described in U.S. Pat. No. 6,315,750 by J. T. Gray. The US patent describes a lumbar traction device that is used while the patient is in a seated position and comprises a pair of rigid side members that, when in use, extend from under the arms of the user to a chair. Extending between the side members is a slidably mounted girdle that slides along the rigid members in a vertical direction. The girdle is secured in a desired vertical position by load bearing straps that pass over the top of the rigid side members and are secured to the girdle by way of hook and loop type fasteners. When in use, the girdle is suspended by the straps and the portion of the user's weight that is supported by the girdle is removed from the lumbar portion of the user's spine.

In our view one of the disadvantages of the device described in the US patent is that when the device is worn by the patient the device is a major obstacle to the mobility of the user and would prevent the user from readily moving between seated and standing positions.

Other possible difficulties with the device described in the US patent is that the rigid side members may be relatively unstable and prone to movement or swaying in a side-to-side direction or in a back-and-forth direction. In addition when the device is in use, the bottoms of the rigid side members will be prone to moving outwardly away from each other and the tops of the side member will be prone to moving inwardly toward each other. The free movement of the rigid side members is likely to create discomfort for the user by the rigid side members bearing against the rib cage of the user.

It is an object of the present invention to provide an alternative lumbar traction device.

SUMMARY OF THE PRESENT INVENTION

According to the present invention there is provided a device worn by a user to reduce loading of the lumbar region or place the lumbar region in traction when worn by a user in a sitting orientation, the device including:
i) a harness or girdle that is fitted about the torso region of a user; and
ii) a support assembly to which the harness is detachably connected and, when in use, a user wearing the harness is supported in an elevated position with their buttock either completely or partially lifted while in a sitting orientation,
wherein the harness and support assembly have co-operating formations that interconnect such that, when in use, the weight of the user assists in retaining the co-operating formations in an interconnected relationship.

One of the advantages of the present invention is that the harness can be readily detached from the support assembly by the weight of the user being removed from the co-operating formations, for example, by the user moving from a sitting orientation to standing.

The phrase to "... place the lumbar region in traction..." or variations thereof throughout this specification means that the lumbar region is subject to some level of tension or tensile force as opposed to compressive forces or loads. Similarly, the phrase to "... reduce loading of the lumbar region" or variations thereof throughout this specification means that the usual loads on the lumbar region, for example, when the user is in the conventional sitting position, have been reduced by the device.

Preferably, the co-operating formations detachably interconnect the support assembly and harness at two or more attachment points, and the co-operating formations are in the form of keyed formations or intercoupling formations that interconnect and disconnect by movement of the formations relative to each other in an upward and/or downward direction.

According to one embodiment the keyed or intercoupling formations may be co-operating dovetail formations, co-operating male and female formations such as a ball and socket formations, or co-operating slot and pin head formations. According to a preferred embodiment, the formations are in the form of a hook or rod that engages a contact surface such as a recess, indentation or opening in the support assembly intended to receive the hook or rod.

According to the present invention there is provided a device worn by a user to reduce loading of the lumbar region or place the lumbar region in traction when worn by a user in a sitting orientation, the device including:
i) a harness or girdle that is fitted about the torso region of a user; and
ii) a support assembly to which the harness is detachably connected and, when in use, a user wearing the harness is supported in an elevated position with their buttock either completely or partially lifted while in a sitting orientation,
wherein the support assembly includes a height adjustor that locates that harness at one of several predefined or known locations or elevations on the support assembly.

According to one embodiment, the support assembly includes two side legs with one of the legs located either side of the user, and the height adjustor is in the form of a series of single point attachments on each of the legs at corresponding heights such that, when in use, the harness is able to be located in a horizontal orientation by connection to pairs of points attachments on the legs.

According to an alternative preferred embodiment, the support assembly includes two side legs to which the harness is attached, and the height adjustor enables the height or length of each leg to be adjusted.

According to the present invention there is provided a device worn by a user to reduce loading of the lumbar region or place the lumbar region in traction when worn by a user in a sitting orientation, the device including:
i) a harness or girdle that is fitted about the torso region of a user; and
ii) a support assembly to which the harness is detachably connected and, when in use, a user wearing the harness is supported in an elevated position with their buttock either completely or partially lifted while in a sitting orientation, wherein the support assembly includes adjustable legs that are capable of being extended and retracted as desired to change the degree of elevation of the user.

One of the benefits of the present invention is that the total length of the legs can be adjusted to suit people of various heights and ages, from children to fully grown adults.

According to the present invention there is provided a device worn by a user to reduce loading of the lumbar region or place the lumbar region in traction when worn by a user in a sitting orientation, the device including:

i) a harness or girdle that is fitted about the torso region of a user; and a support assembly to which the harness is detachably connected and, when in use, a user wearing the harness is supported in an elevated position with their buttock either completely or partially lifted while in a sitting orientation, wherein the support assembly includes two legs and a foot member interconnecting lower portions of the legs and thereby securing the lower ends of the legs in spaced relationship.

According to one embodiment, the foot member and/or the lower end of the legs is adapted to such that the upper end of the legs are to some degree held apart by the foot.

According to the present invention there is provided support assembly for supporting a harness and girdle worn about the torso region of a user so as to reduce loading of the lumbar region of user or place the lumbar region in traction when the user is in a sitting orientation, the support assembly including:

i) two legs and a foot member interconnecting lower portions of the legs so as to hold the legs apart in spaced relationship;

ii) a pair of coupling formations, one on each leg, whereby when in use, the coupling formations are adapted for connected with co-operating formations of a harness or girdle worn by a user so that user is supported in an elevated position with their buttock either completely or partially lifted while in a sitting orientation, wherein the legs are adjustable legs and are capable of being extended and retracted as desired to change the degree of elevation of the user.

According to the present invention there is provided a harness or girdle that is worn about the torso of a user, the harness having:

i) a back panel and two side panels that are each adjustably connected to the back panel so that the combined length of the back and side panels can be adjusted to fitted about the torso region of users of different sizes; and ii) two hook formations that protrude outwardly from the harness and which are received by co-operating supports on which the hook formations are able to be seated so as to locate the user wearing the harness in an elevated suspended position with their buttock either completely or partially lifted while the user is in a sitting orientation, the hook formations being configured to allow free movement in an upward direction so that the user can move between a sitting position in which the coupling formation is seated and a standing position.

DETAILED DESCRIPTION

Preferably the device includes an adjustor for adjusting the length of the legs. The adjustor may be an actuator that changes the length of the legs, including hydraulic, pneumatic or electric rams. However preferably, the adjustor is one that is hand operated and may include a screw thread mechanism, or any other manually operated mechanism.

Preferably, the legs each include an upper portion and a lower portion that are moveable relative to each other and change the overall length of the legs.

Preferably, the adjustor allows the upper and lower leg portions to interfit in mating relationship. For example, the upper and lower portions of the legs may interfit in a telescopic manner in which one portion fits inside the other. A locking device such as a hole and pin arrangement may be used to the fix the relative positions of the upper and lower portions. Preferably, the adjustor comprises the upper and lower leg portions having mating interfaces that resist relative upward and downward movement of the upper and lower leg portions when the device is located in an upright, in use, orientation.

Preferably, the adjustor enables the height or length of the legs of the support assembly to be operated independently of, and irrespective of whether the harness is supported by the support assembly.

Preferably, the mating interfaces comprise sets of the ridges or crests on the upper and lower portions in which the ridges or crests extend in a direction lateral to the direction of the legs. The ridges and crests on the lower leg portion interfit with the crest and ridges of the upper leg portion respectively. The ridges and crests are an example of a mechanical interface between the upper and lower leg portions that prevents the upper and lower leg portions from moving relative to each other when in mating relationship.

Although it is possible that the crests and ridges may have any profile including triangular or squared profiles, preferably, the sets of ridges and crests have a wave, semi-circular or sinusoidal profile. One of the advantages of using crest and ridge interfaces is that it allows the position of the upper and lower portions of the legs to be easy determined by observing the number of the ridges or crests located above or below crests or ridges that are not aligned in mating relationship.

Preferably, the support assembly further includes a locking system for holding the upper and lower portions together in mating relationship.

Preferably, the locking system includes one or more than one slot in either one of the upper or lower leg portions, and one or more than one post or stump on the other upper or lower leg portions that protrudes through the slot and a locking member, fitted to the stump, engages the upper and/or the lower portions to prevent the portions from disengaging from the mating relationship when the device is in use.

Preferably, the locking member is pivotally mounted to the stump or post and is in the form of an over centre cam lever that is pivoted between an inoperative position in which the upper and lower leg portions can be moved relative to each other to allow the length of the legs to the adjusted and an operative position in which the upper and lower portions are held in an engaged mating relationships.

Preferably, the locking member includes a handle which is pivoted between an upper position in which the over centre cam is inoperative and a lower position in which the over centre cam is in an engaged operative position. Preferably, the handle protrudes outwardly from the sides of the device when in an operative position and includes a stop to prevent the handle from moving further downward beyond the operative position such that the user can use the handle, when located in an operative position, to assist themselves in moving from a standing position into a sitting orientation to use the device, or to assist in moving from a sitting orientation while using the device to a standing position.

In other words, the handle can be used to help a user into and out of a sitting orientation to facilitate use of the device.

In another embodiment another handle or arm rest, extends from an upper end of the upper leg portion and can assist a user in raising or lowering themselves between seated and standing orientations.

Preferably, the upper leg portions are located on the inside of the lower leg portions and the locking system is in the form of the lower leg portions including two slots and the upper leg portion each include two stumps, each stump extending through one of the slots and the locking member is pivotally mounted to the posts.

Preferably, the harness is detachably connected to the support assembly by way of a single point attachment to each of the legs. Suitably, the each attachment point comprises co-operation formations such as a keyed formation or an inter-coupling formation.

Preferably, the weight of the user assists in retaining the co-operating formations in an interconnected relationship.

Even more preferably, the harness is detachably connected to the support assembly by way of a hook formation that engages the support assembly. In the situation in which the hook formation faces downwardly, a user wearing the harness can be readily disconnect the harness by moving from a sitting position to standing.

Preferably, the support assembly includes a foot member that interconnects and holds a lower portion of the legs at spacing relationship.

Preferably, the support assembly further includes a foot adjustor for adjusting the spacing at which the lower portion of the legs are held apart.

Although the foot adjustor may be provided by any form including threaded and screw type mechanisms, ram type mechanisms driven electrically, hydraulically, pneumatically or by any other power source, preferably, the foot adjustor includes a series of openings or holes into which a pin can be removably placed in order to secure the position of the foot member relative to the legs.

Preferably, the harness has a modular structure comprising a back panel and two side panels that are each adjustably connected to the back panel so that the combined length of the back and side panels can be adjusted to fitted about the torso region of users of different sizes.

Preferably the side and back panels are detachable and can interconnect at different positions relative to each other by sets of co-operating press studs located at different positions on the back and side panels.

Even more preferably, the harness further includes a front panel that overlaps with the side panels. Preferably, the side panels interconnected with the front panel by means of hook and loop fasteners.

Preferably, the side panels are also interconnected by one or more than one strap or buckle.

Preferably, the harness further includes an inflatable container such as a cushion, pillow or bag that is incorporated of fitted to the back panel. An advantage provided by the inflatable container is that can mould itself to the particular shape of the torso of the user and thereby improve comfort.

Preferably, the device further includes a container, cushion, pillow or bag beneath the buttock region of the user which can be inflated to reduce the level of traction being applied to the user or deflated to increase the level of traction being applied to the user. In other words, the container, cushion, pillow or bag is designed to be able to carry a portion of the weight of the user.

BRIEF DESCRIPTION OF THE DRAWINGS

A preferred embodiment of the present invention will now be described with reference to the accompanying drawings, of which.

A PREFERRED EMBODIMENT

Figure 1:
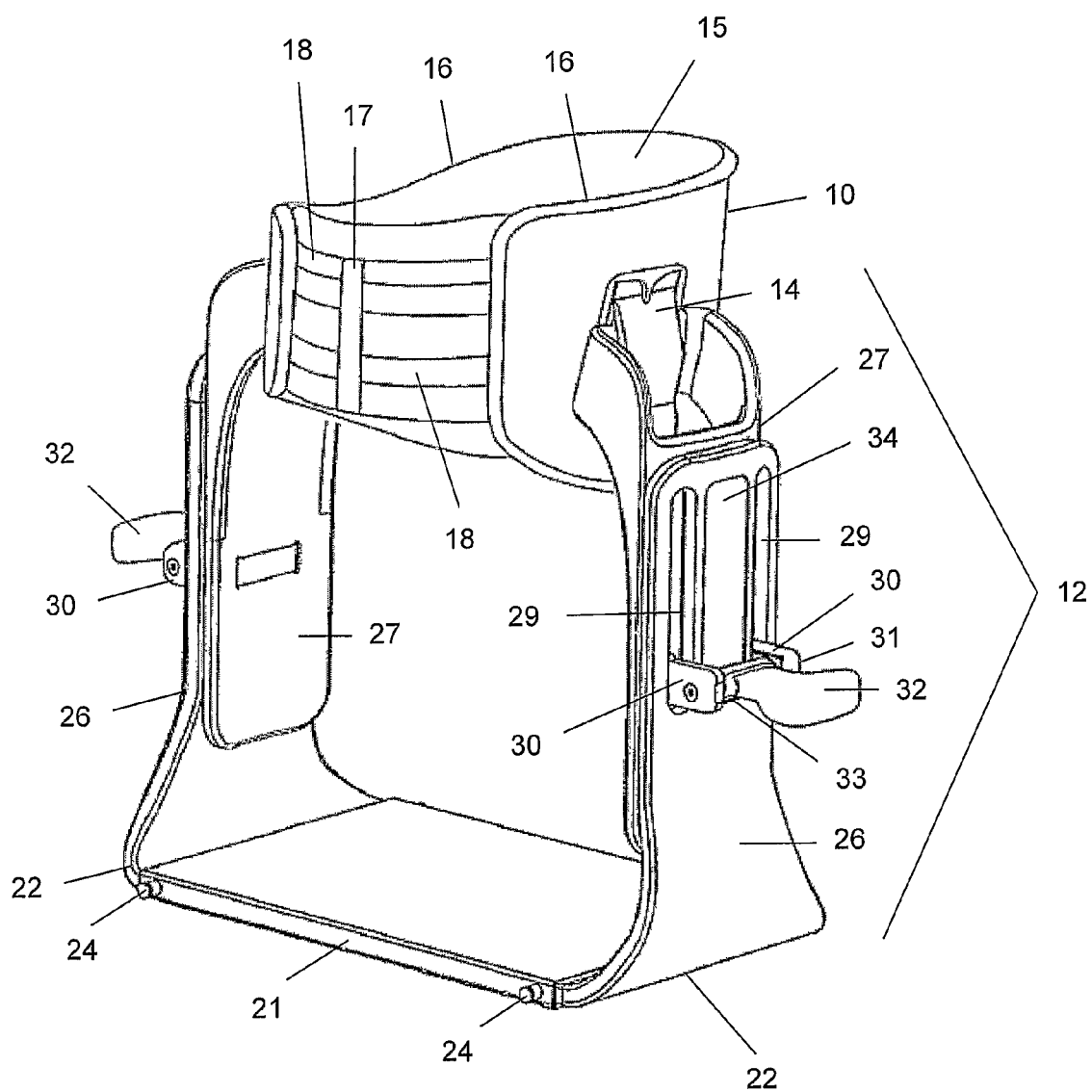
FIG. 1 is a perspective view of a device that can be worn by a user to place the lumbar spinal region of a user in traction when the user is in a sitting orientation.
Figure 2:
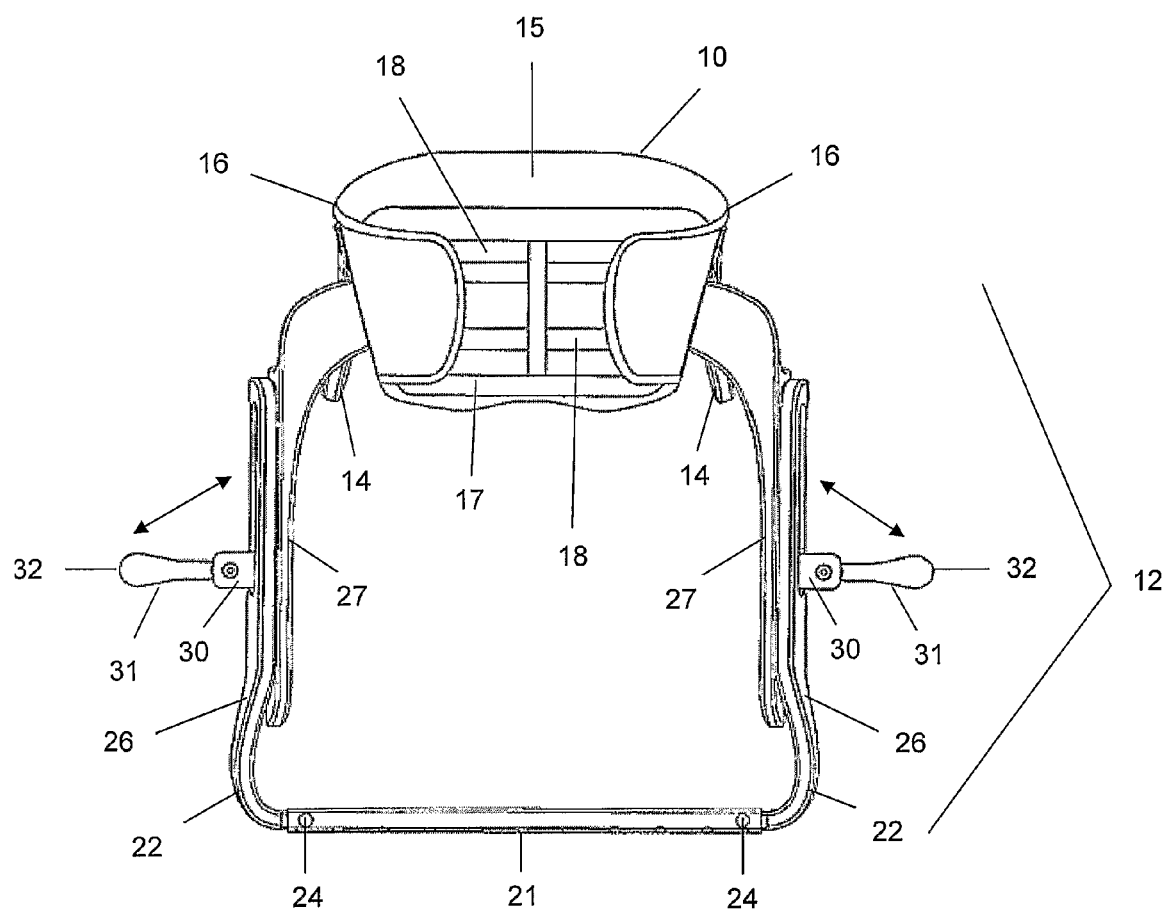
FIG. 2 is a front view of the device shown in FIG. 1.
Figure 3:
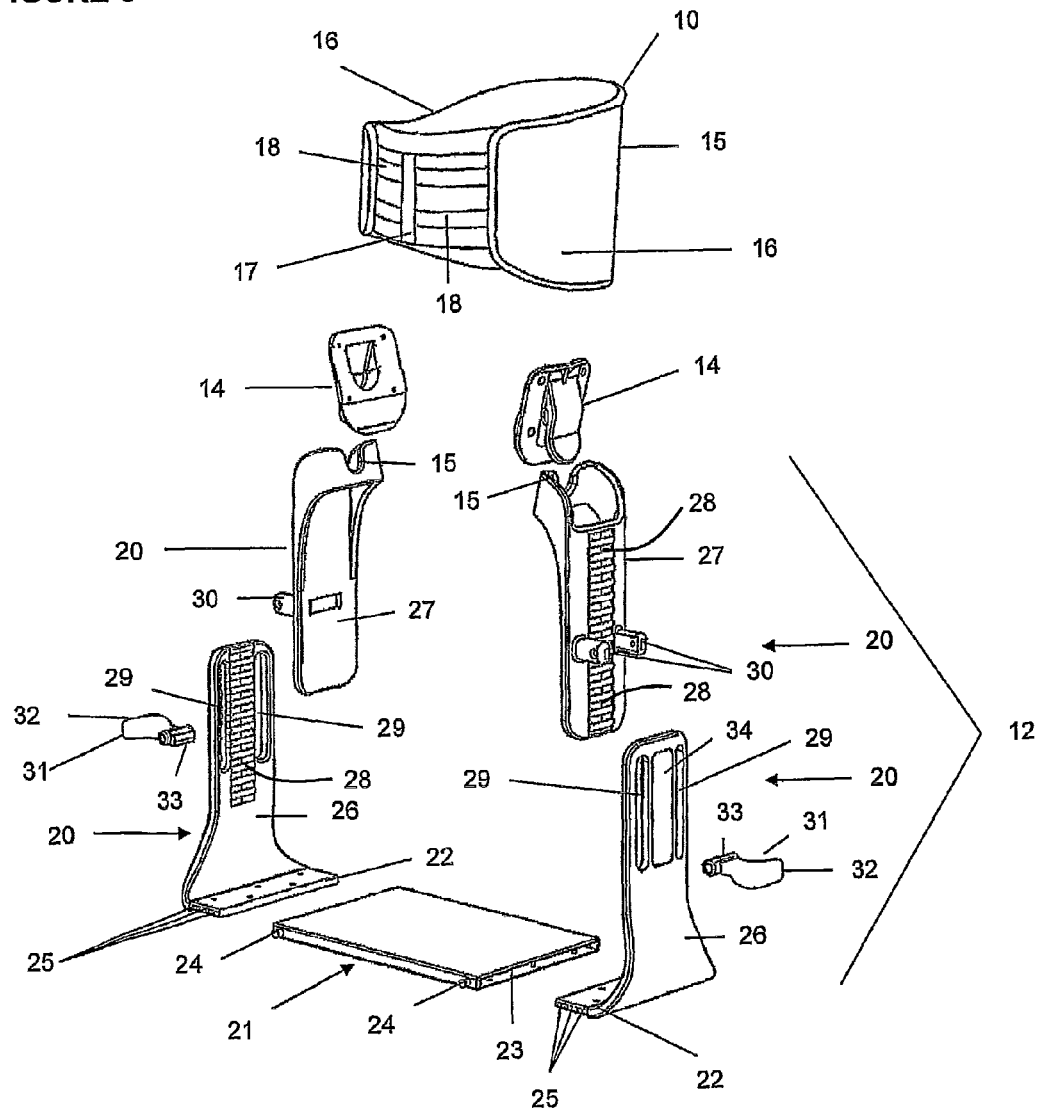
FIG. 3 is an exploded view of the major components of the device shown in FIGS. 2 and 3.
Figure 4:
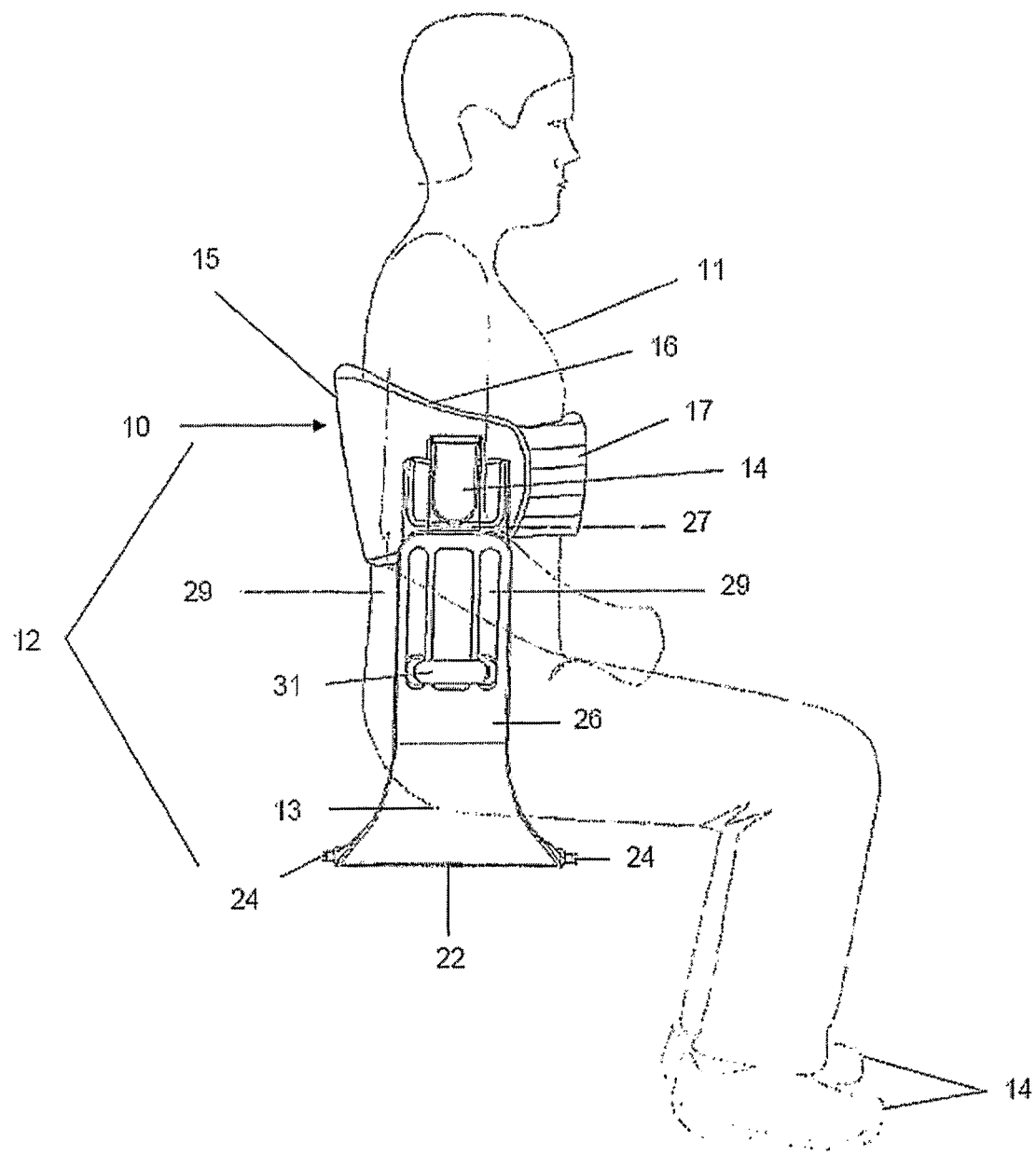
FIG. 4 is a side view of the device shown in FIGS. 1 to 3 with a person using the device to place the lumbar region of their spinal in traction using their own body weight.

With reference to the figures, the preferred embodiment as shown in FIGS. 1 to 4 is in the form of a traction device comprising an adjustable harness 10 that encircles the torso region of a user 11 and an adjustable support assembly 12 that supports the harness 10 and a user 11 wearing the harness 10 in a suspended position such that the weight of the user 11 below the harness 10 places the lumbar spinal region of the user 11 in a level of traction. In practice, the user 11 can manage the level of traction by either i) changing the height at which the harness 10 is supported by the support assembly 12 and thus whether the buttocks 13 of the user 11 is partially or completely lifted; or ii) the user 11 supports part of their lower body weight by placing their feet 14 on the ground and, optionally, pushing down on the ground.

One of several advantages provided by the preferred embodiment is that the harness 11 and support assembly 12 have co-operating formations, which in the case of the preferred embodiment are hook formations 14 extending outwardly of the harness 11 and co-operating recesses 15 in the support assembly 12 that receive the hook formations 14. When in use, the hook formations 14 of the harness 10 maintain engagement with the support assembly 12 in a downward direction at least in part on account of the weight of the user. In other words, in order to detach the harness 10 from the support assembly 12, the user can detach the formations by moving from a sitting orientation to standing.

Although not shown in detail in the drawings, the harness 10 is preferably a modular structure having a back panel 15, two side panels 16 and a front panel 17. The back and side panels are interconnected by way of a series of press studs that allow the panels to be interconnected at various positions and thereby allow the combined length of the back and side panels to be adjusted to suit different torsos sizes. The loose ends of the side panels i.e., the ends not connected to the back panel 15 overlap and engage the front panel 17 by way of hook and loop fasteners. Additional straps 18 having slidable adjustment buckles also interconnect the side panels 16 across the front of the harness 10 to enable finer adjustment of pressure applied to the torso region. Ideally, the back and side panels 15 and 16 are made from a cushioned fabric and an inner reinforcing plastic that helps provide some rigidity to the harness 10 in the vertical direction. The reinforced plastic may be any suitable material.

In addition, the panels 15, 16 and 17 are shaped to provide the greatest possible comfort for the user 11 and, in particular, the back panel 15 has a taller vertical profile than the side and front panels 16 and 17 to provide support to the spine of the user 11 above the lumbar region. The vertical dimension of the side panels 16 preferably tapers in a direction toward the free ends of the side panels 16. Although not shown in the figures, the upper edge of the front panel 17 may also include cut outs to prevent breast discomfort for female users 11. In addition, one or more of the panels 15, 16 and 17, and suitably the back panel 15 may incorporate an inflatable air bag or cushion to help provide support and comfort when in use.

The base support assembly 12 includes a pair of side legs 20 that are interconnected by a rectangular foot member 21. The lower end of each leg comprises an inwardly turned flange 22 that is received by openings 23 at either end of the foot member 21. The foot member 21 includes a set of four locking members 24, one of each being located at the corner of the foot member 24. Each locking member 24 comprises a locking bolt or pin that is operated between: i) an inward locking position in which the locking pin is received in one or of several side apertures 25 in the lower flange 22 of the legs 20; and ii) an outward unlocking position in which the flanges 22 of the legs 20 can be slid inward and outward. The locking bolt or pin also includes an outer button that is hand operated and an internal spring that biases the locking bolt toward the inner locking position. In use, the foot member 21 is slid over the flange 22 and the locking members 24 operated to fix the spacing of the legs 20 to the desired width depending on the width and size of the user 11.

With regard to the legs 20, each comprises a lower leg portion 26 from which the inwardly curled flange 22 extends and an upper leg portion 27 located on the inside of the lower leg portion 26. The upper leg portion 27 is adjustable along the inside of the lower leg portion 26 and thereby enables the device to cater for people of varying heights. The upper and lower leg portions 26, 27 each include sets of ridges or corrugations 28 in the form of evenly sized waves that are equally spaced on both the lower and upper leg portions 26, 27. The corrugations 28 are oriented in a direction transverse or at right angles to the direct in which the legs 20 are adjusted and thereby provide a mechanical interface between the upper and lower leg portions 26, 27. When in use, the corrugations 28 of the upper and lower leg portions 26, 27 interfit in mating relationship in which the troughs of the lower leg portion 26 receive the crests of the upper legs portion 27 and vice versa, with the troughs of the upper leg portion 26 received by the crests of the lower leg portion 27.

The corrugations 28 of the upper and lower legs portions are held together in a mating relationship by a quick release locking mechanism. Specifically, each of the lower leg portions 26 include two slots 29 running in a length wise direction and the upper leg portions 27 each include two stump formations 30 that extend through the slots 29 in the lower leg portion 26. Interconnecting the stumps 30 on the outside of the lower leg portions 26 is an over centre cam lever 31. The lever 31 has a handle portion 32 and an engaging surface 33 in the form of an asymmetric roller or cylinder that is pivotally mounted to the stumps 30. The handle 32 and engaging surface 33 of the cam lever 31 are configured such that when the handle 32 of the lever 31 is located in an upward position as shown by the direction of the arrows in FIG. 2, the engaging cam surface is disengaged, allowing relative movement between the upper and lower leg portions 26, 27. When the handle is located in a downward position, the cam surface 33 engages the outer face 34 of the lower leg portion 26, forcing the upper and lower leg portions 26, 27 into mating relationship and preventing relative movement between the upper and lower leg portions 26, 27.

FIGS. 1 to 4 illustrate the handle 32 located in a downward position, and as can be seen the handle 32 protrudes outwardly perpendicular to the legs 20. In addition, the handle 32 is prevented by a stop from further pivoting downwardly from the position shown in the figures. As a result, with the handles 32 in the position shown in the figures enable a user 11 to use the handles 32 as a basis on which help lower themselves from a standing position into a lower sitting position or vice versa.

Figure 5:
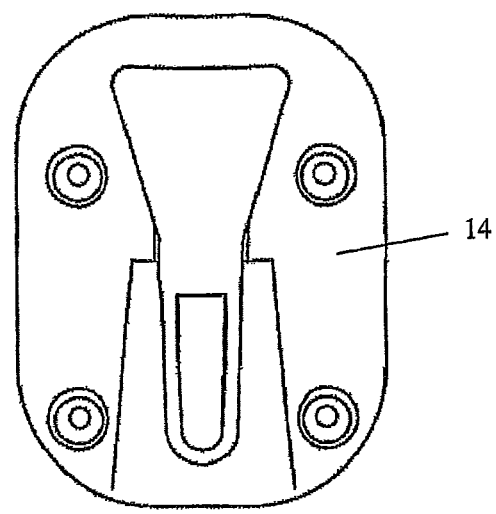
FIG. 5 is a front view of two interfitting parts of a device that can be used to place the lumbar region of a user in traction according to an alternative embodiment of the present invention.
Figure 5:
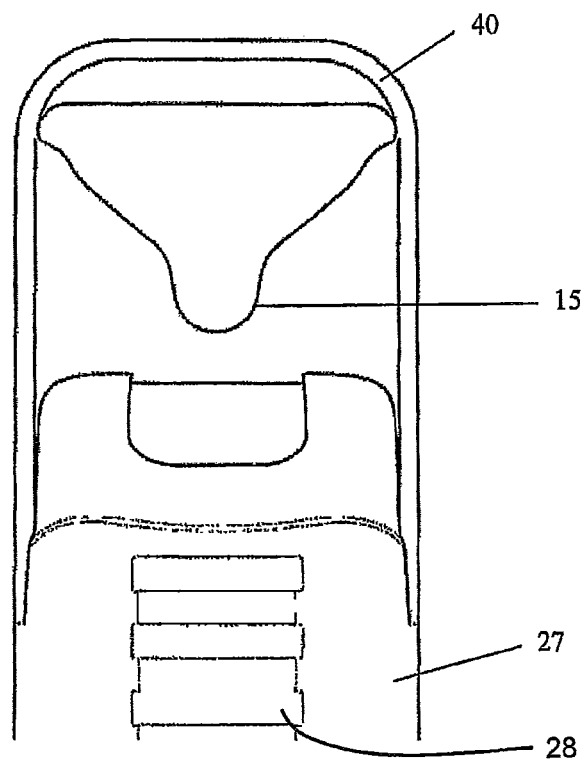

FIG. 5 illustrates an alternative embodiment of a section of an upper leg portion 27 of a support assembly and a hook formation 14 that is essentially the same as the hook formation 14 shown in FIGS. 1 to 4. Although the entire support assembly and lower leg portions are not shown in FIG. 5, it will be appreciated that the upper leg portion 27 forms a part of support assembly similar to that shown in FIGS. 1 to 4 and can be used in combination with a lower leg portion. Moreover, two of the upper leg portions 27 will be used in conjunction with lower leg portions, on each side of a user.

The upper leg portion 27 shown in FIG. 5 includes a handle 40 that extends above a recess 15 that receives the hook formation 14. The purpose of the handle 40 is to allow users to lower themselves into position, and in particular the hook formation 14 that extends from a harness (not shown) worn by a user into the recess 14. The handle formation 14 allows a user to do this conveniently without placing their hands on the recess 15.

In addition, although not shown in FIG. 5, the handle 40 may also be used instead of the over centre lever 31 being used as a handle as described with reference to FIGS. 1 to 4. In this connection, the over centre lever 31 may thus be designed such that a cam surface of the lever is engage when the lever is pivoted downwardly or upwardly so as to be oriented parallel to the upper and lower leg portions. Similarly, the lever 31 may be disengaged, allowing free relative movement of the upper and lower leg portions when the lever extends outwardly or perpendicular to the upper and/or lower leg portions.

Those skilled in the art of the present invention will appreciate that many modifications and variations may be made to the preferred embodiment without departing from the spirit and scope of the preferred embodiment described above.

For example, although it is preferred that the legs and foot member of the support assembly may be made from any suitable injection moulded plastic materials, it is possible that the legs and foot member may be may of any materials including metal allow materials.

The claims defining the invention are as follows:

1. A device that is able to be worn by a user to place a lumbar spinal region of the user in traction when the user is in a sitting orientation, the device including:
   i) a harness that is adapted to be fitted about a torso region of the user; and
   ii) a support assembly having two legs and a foot member interconnecting lower portions of the two legs and thereby securing lower ends of the legs in spaced relationship,
   wherein the harness and the two legs are detachably connected by way of co-operating formations that interconnect and disconnect by movement of the co-operating formations in an upward or downward direction relative to each other, and
   wherein, in use, weight of the user assists in retaining the co-operating formations in an interconnected relationship and the harness is configured to be detached from the support assembly solely by the user moving from the sitting orientation to standing when the harness is fitted about the torso region of the user, and wherein, in use, the support assembly supports the harness and the user in a suspended position with a buttock of the user being either completely or partially lifted while in the sitting orientation such that weight of the user below the harness places the lumbar spinal region of the user in a level of traction.

2. The device according to claim 1, wherein the two legs are adjustable and capable of being extended and retracted as desired to change a degree of elevation of the user.

3. The device according to claim 2, wherein the two legs include each of upper and lower leg portions having mating interfaces which when held together in mating relationship prevent extension and retraction of the two legs.

4. The device according to claim 3, wherein the support assembly further includes a locking system for holding each of the upper and lower leg portions together in mating relationship, and the locking system includes at least one slot in either one of the upper or lower leg portions, and at least one post on the other of the upper or lower leg portions that protrudes through the at least one slot and a locking member, fitted to the post, that engages the respective upper or lower leg portion having the at least one slot and which can be operated to retain the upper and lower leg portions in mating relationship.

5. The device according to claim 4, wherein the locking member includes a handle and an asymmetric surface pivotally mounted to the at least one post, and the handle can be pivoted between an upper position in which the asymmetric surface is in a disengaged inoperative position in which it is spaced from the respective upper or lower leg portion having the slot, and a lower position in which the asymmetric surface is located in an engaged operative position in which the asymmetric surface bears against the respective upper or lower leg portion having at least one the slot.

6. The device according to claim 3, wherein the mating interfaces comprise sets of ridges or crests on the upper and lower leg portions and the ridges or crests extend laterally to the length of the two legs.

7. The device according to claim 3, wherein an upper end of the upper leg portions includes a handle or arm rest which can be used to assist the user in raising or lowering themselves between seated and standing orientations.

8. The device according to claim 2, wherein the device includes an adjustor for adjusting a length of the two legs and the adjustor is a hand or manually operated mechanism.

9. The device according to claim 8, wherein the adjustor enables height or the length of the two legs of the support assembly to be operated independently of, and irrespective of whether the harness is attached to the support assembly.

10. The device according to claim 1, wherein the harness has a back panel and two side panels that are each adjustably connected to the back panel so that a combined length of the back panel and the two side panels can be adjusted to fit about torso regions of users of different sizes.

11. The device according to claim 10, wherein the harness further includes a front panel that overlaps with the two side panels and is interconnected with the two side panels by means of hook and loop fasteners.

12. The device according to claim 11, wherein the two side panels are also interconnected by one or more than one strap or buckle.

13. The device according to claim 10, wherein the two side panels and the back panel are detachable and can interconnect at different positions relative to each other by sets of co-operating press studs located at different positions on the back panel and the two side panels.

14. The device according to claim 10, wherein the harness further includes an inflatable bladder such as a cushion, pillow or bag that is incorporated in or fitted to the back panel.

15. The device according to claim 1, wherein the co-operating formations are formed as keyed formations or intercoupling formations that interconnect and disconnect by movement of the co-operating formations relative to each other in an upward or direction when the device is in an upright orientation.

16. The device according to claim 15, wherein the keyed formations or intercoupling formations are co-operating male and female formations.

17. The device according to claim 15, wherein the keyed formations or intercoupling formations are a hook or rod on the harness that is received by an upwardly facing opening in the support assembly.

18. The device according to claim 1, wherein the support assembly further includes a foot adjustor for adjusting spacing at which the lower portion of the two legs are held apart.

19. The device according to claim 18, wherein the foot adjustor includes a series of openings or holes in the foot member and the lower ends of the two legs into which a pin can be removably placed in order to secure a position of the foot member relative to the two legs.

20. The device according to claim 1, wherein the support assembly is adapted so that upper end of the two legs resist movement toward each other when subjected to load by the user.

21. The device according to claim 1, wherein the device further includes an inflatable bladder that can be located beneath a buttock region of the user and a degree of inflation of the inflatable bladder can be used to further control the level of traction.

22. A device that is able to be worn by a user to place a lumbar spinal region of the user in traction when the user is in a sitting orientation, the device including:
  i) a harness that is adapted to be fitted about a torso region of the user; and
  ii) a support assembly to which the harness is detachably connected, wherein the support assembly includes
    a) adjustable legs that are capable of being extended and retracted as desired to change a degree of elevation of the user, and
    b) a foot member interconnecting lower portions of the adjustable legs and thereby securing lower ends of the adjustable legs in spaced relationship,
  wherein the harness and the adjustable legs are detachably connected by way of co-operating formations that interconnect and disconnect by movement of the co-operating formations in an upward or downward direction relative to each other, and wherein, in use, weight of the user assists in retaining the co-operating formations in an interconnected relationship and the harness is configured to be detached from the support assembly solely by the user moving from the sitting orientation to standing when the harness is fitted about the torso region of the user, and wherein, in use, the support assembly supports the harness and the user in a suspended position with a buttock of the user being either completely or partially lifted while in the sitting orientation such that weight of the user below the harness places the lumbar spinal region of the user in a level of traction.

23. A device that is able to be worn by a user to place a lumbar spinal region of the user in traction when the user is in a sitting orientation, the device including:
  i) a harness that is adapted to be fitted about a torso region of the user; and
  ii) a support assembly to which the harness is detachably connected, wherein the support assembly includes
    a) adjustable legs that are capable of being extended and retracted so that, when in use, a degree of elevation of the user can be adjusted by adjusting the adjustable legs, and b) a foot member interconnecting lower portions of the adjustable legs that secures lower ends of the adjustable legs in spaced relationship, wherein the adjustable legs and foot member are adapted so that upper ends of the adjustable legs resist movement toward each other when subjected to load by the user, and wherein the harness and the adjustable legs are detachably connected by way of co-operating keyed formations that interconnect and disconnect by movement of the co-operating keyed formations in an upward or downward direction relative to each other, and wherein, in use, weight of the user assists in retaining the co-operating keyed formations in an interconnected relationship and the harness is configured to be detached from the support assembly solely by the user moving from the sitting orientation to standing when the harness is fitted about the torso region of the user, and wherein, in use, the support assembly supports the harness and the user in a suspended position with a buttock of the user being either completely or partially lifted while in the sitting orientation such that weight of the user below the harness places the lumbar spinal region of the user in a level of traction.

\* \* \* \* \*

UNITED STATES PATENT AND TRADEMARK OFFICE
CERTIFICATE OF CORRECTION

| | | |
|---|---|---|
| PATENT NO. | : 8,652,081 B2 | Page 1 of 1 |
| APPLICATION NO. | : 12/740494 | |
| DATED | : February 18, 2014 | |
| INVENTOR(S) | : Marcus Andrew Rawlings | |

It is certified that error appears in the above-identified patent and that said Letters Patent is hereby corrected as shown below:

In the Claims

Column 8, Line 49, Claim 1, before "legs" insert -- two --

Column 9, Line 4, Claim 3, after "wherein" insert -- each of --

Column 9, Line 5, Claim 3, after "include" delete "each of"

Column 9, Line 16, Claim 4, before "post" insert -- at least one --

Column 10, Line 2, Claim 15, after "or" insert -- downward --

Signed and Sealed this
Third Day of June, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,652,081 B2
APPLICATION NO. : 12/740494
DATED : February 18, 2014
INVENTOR(S) : Marcus Andrew Rawlings It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 515 days.

Signed and Sealed this

Twenty-ninth Day of September, 2015

Michelle K. Lee
*Director of the United States Patent and Trademark Office*